(12) United States Patent
Ciambecchini et al.

(10) Patent No.: US 8,981,090 B2
(45) Date of Patent: Mar. 17, 2015

(54) PROCESS FOR THE SYNTHESIS OF PEMETREXED DISODIUM SALT

(75) Inventors: Umberto Ciambecchini, Patricia (IT); Stefano Turchetta, Patricia (IT); Maurizio Zenoni, Patricia (IT); Lorenzo De Ferra, Patricia (IT); Paolo Brandi, Patricia (IT)

(73) Assignee: Chemi S.p.A., Cinisello Balsamo (IT)

( * ) Notice: Subject to any disclaimer, the term of this patent is extended or adjusted under 35 U.S.C. 154(b) by 735 days.

(21) Appl. No.: 13/176,199

(22) Filed: Jul. 5, 2011

(65) Prior Publication Data

US 2012/0172595 A1    Jul. 5, 2012

(30) Foreign Application Priority Data

Jul. 22, 2010   (IT) .............................. MI2010A1351

(51) Int. Cl.
*C07D 487/04*    (2006.01)
(52) U.S. Cl.
CPC ................................... *C07D 487/04* (2013.01)
USPC ........................................................ 544/280
(58) Field of Classification Search
CPC .................................................... C07D 487/04
See application file for complete search history.

(56) References Cited

U.S. PATENT DOCUMENTS

| | | | |
|---|---|---|---|
| 5,416,211 A | 5/1995 | Barnett et al. | |
| 6,013,828 A * | 1/2000 | Kjell et al. | ...................... 560/11 |
| 2001/0011142 A1 | 8/2001 | Kjell | |

FOREIGN PATENT DOCUMENTS

WO    WO 2008021405 A1 *   2/2008

OTHER PUBLICATIONS

Dupont. "Solvents." (C) Aug. 30, 2009. Available from: <http://web.archive.org/web/20090830043927/http://www2.dupont.com/Methylamines/en_US/uses_apps/solvents.html >.*
Barnett, C. J. et al., "A Practical Synthesis of Multitargeted Antifolate LY231514" Organic Process Research and Development, Cambridge, GB, vol. 3, No. 3, Jan. 1, 1999, pp. 184-188, XP000982091, DOI: D0I:10.2021/0P9802172.
Graul, A. et al., "Pemetrexed Disodium. Antineoplastic antifolate," Drugs of the Future, Prous Science, ES, vol. 23, No. 5, Jan. 1, 1998, pp. 498-507, XP002610115, ISSN:0377-8282.

European Search Report dated Mar. 1, 2011 issued in IT Application No. MI20101351.

* cited by examiner

Primary Examiner — Andrew D Kosar
Assistant Examiner — John S Kenyon
(74) *Attorney, Agent, or Firm* — Silvia Salvadori, P.C.

(57) ABSTRACT

The present invention relates to a novel process for the preparation of pemetrexed diethyl ester 2

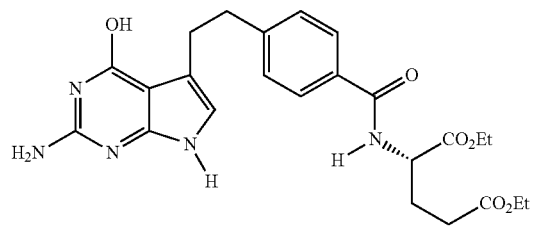

by purifying the mixture obtainable by reacting compounds 1 and 1a in the presence of a chemical agent capable of promoting the formation of a peptide bond in an aprotic organic solvent

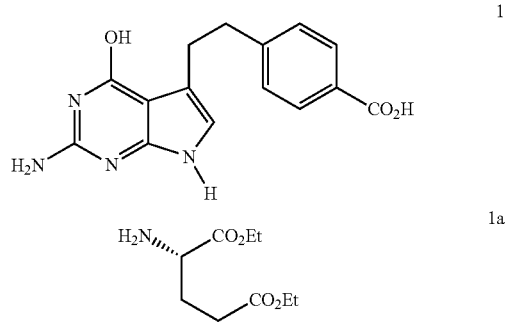

characterized in that the mixture is subjected to the following steps:
a) washing with a basic aqueous solution;
b) concentration of the organic phase;
c) addition of a polar organic solvent and/or a mixture of polar organic solvents;
d) precipitation of the pemetrexed diethyl ester 2.

22 Claims, 6 Drawing Sheets

PROCESS FOR THE SYNTHESIS OF PEMETREXED DISODIUM SALT

CROSS REFERENCE TO RELATED APPLICATIONS

This application claims priority to and the benefit of Italian application MI2010A001351, the content of which is hereby incorporated by reference in its entirety.

SUMMARY OF THE INVENTION

The present invention relates to a novel process for the preparation of pemetrexed diethyl ester 2 which comprises the step of purifying the mixture obtainable by reacting compounds 1 and 1a in the presence of a chemical agent capable of promoting the formation of a peptide bond in an aprotic organic solvent characterized in that the mixture is subjected to the following steps:
a) washing with a basic aqueous solution;
b) concentration of the organic phase;
c) addition of a polar organic solvent and/or a mixture of polar organic solvents;
d) precipitation of the pemetrexed diethyl ester 2.

The present invention relates also to a process for the preparation of the disodium salt 5 comprising the above-mentioned process for the preparation of pemetrexed diethyl ester 2. A further subject of the present invention is the crystalline form of pemetrexed diethyl ester 2.

DETAILED DESCRIPTION OF THE INVENTION

Pemetrexed is the international non-proprietary name (INN) of the active ingredient N-[4-[2-(2-amino-4,7-dihydro-4-oxo-1H-pyrrolo[2,3-d]pyrimidin-5-yl)ethyl]benzoyl]-L-glutamic acid, compound 4:

The related disodium salt, compound 5, is the active ingredient contained in the pharmaceutical specialty ALIMTA® which is widely used in the treatment of non-small cell lung cancer (NSCLC) and malignant pleural mesothelioma and is under investigation for application in the therapy of other oncological pathologies.

Pemetrexed belongs to the class of the multitargeted antifolates, that is to say, those anti-tumour active ingredients which act at the level of several folate-dependent enzyme systems involved in the biosynthesis of purines and pyrimidines, the starting point for the biosynthesis of DNA and RNA.

The synthesis of pemetrexed was described for the first time in U.S. Pat. No. 5,344,932. That synthesis starts from the compound 2-amino-7H-pyrrolo[2,3-d]pyrimidin-4-ol which, after the protection of the amine group and the subsequent iodination of the pyrrole ring, is reacted with (S)-dimethyl 2-(4-ethynylbenzamido)pentane dioate. The product of this reaction, after a sequence of simple reactions, is converted into pemetrexed.

According to the more recent U.S. Pat. No. 5,416,211, which is incorporated herein by reference, pemetrexed can be synthesized from 4-[2-(2-amino-4,7-dihydro-4-oxo-1H-pyrrolo[2,3-d]pyrimidin-5-yl)ethyl]benzoic acid of formula 1, obtained from simple precursors, in accordance with the following Scheme 1:

This second method seems to be used also for the industrial preparation of the active ingredient. In fact, the same type of synthesis scheme is also described in C. J. Barnett, T. W. Wilson and M. E. Kobierski, *Org. Proc. Res. & Develop.,* 1999, 3, 184-188, in which the experimental examples refer to a scale of the order of tens of kgs.

In the course of experiments aimed at optimizing and improving the synthesis methodology of Scheme 1, it has now surprisingly been found that pemetrexed diethyl ester 2 can be isolated with high yields in crystalline form having a high degree of purity. This experimental result is entirely unexpected because the only examples from the literature which report on the isolation of pemetrexed diethyl ester 2 as a solid refer to analytical preparations in which the crude compound is purified chromatographically, collected in solution and then isolated by the evaporation of the solvent (E. C. Taylor and B. Liu, *J. Org. Chem.* 2003, 68, 9938-9947 on page 9945, synthesis of compound 25a, m.p. 84-86° C., with IR characterization; C. J. Barnett, T. W. Wilson and M. E. Kobierski, *Org. Proc. Res. & Develop.,* 1999, 3, 184-188 on page 188, synthesis of compound 13, m.p. 169-171).

Therefore, the present invention relates to a novel process for the preparation of pemetrexed diethyl ester 2 which comprises the step of purifying the mixture obtainable by reacting compounds 1 and 1a in the presence of a chemical agent capable of promoting the formation of a peptide bond in an aprotic organic solvent characterized in that the mixture is subjected to the following steps:
a) washing with a basic aqueous solution and subsequent separation of the aqueous phase from the organic phase so obtained;
b) concentration of the organic phase;
c) addition of a polar organic solvent and/or a mixture of polar organic solvents;
d) precipitation of the pemetrexed diethyl ester 2.

According to the invention, the chemical agent capable of promoting the formation of a peptide bond is preferably selected from CDMT (2-chloro-4,6-dimethoxy-1,3,5-triazine), DCC(N,N'-dicyclohexylcarbodiimide), HOBT (hydroxybenzotriazole), EDC (1-ethyl-3-(3-dimethylaminopropyl)carbodiimide), more preferably CDMT (2-chloro-4,6-dimethoxy-1,3,5-triazine).

According to the invention, the aprotic organic solvent is preferably selected from dimethylformamide, dimethylacetamide, dichloromethane, chloroform, ethyl acetate and/or a mixture thereof, and is more preferably a mixture of dimethylformamide and dichloromethane.

According to the invention, the basic aqueous solution is preferably a solution of hydroxides, phosphates, carbonates or bicarbonates of alkali metals or alkaline-earth metals, more preferably of sodium bicarbonate.

The basic aqueous solution has a pH of preferably from 7 to 10, more preferably greater than 7 and less than or equal to 8.

According to the invention, the polar organic solvent is preferably a $C_1$-$C_4$ alcohol, an aliphatic or aromatic ketone, dimethyl sulphoxide or mixtures thereof, more preferably ethanol.

Preferably, from 5 to 15 volumes of polar organic solvent (ml), more preferably from 8 to 12, are used to 1 part by weight of pemetrexed ester 2 titrated in the residue obtained after concentrating the organic phase (g).

According to the invention, the precipitation is preferably effected by heating the mixture obtained in step c) to a temperature of from 50 to 80° C., more preferably from 60 to 65° C., and then cooling it to a temperature of preferably from 0 to 10° C., more preferably to approximately 5° C.; this temperature is preferably maintained for a period of from 1 to 10 hours, preferably 4 hours.

In a preferred embodiment of the present invention, the precipitation takes place at a temperature of from 30 to 60° C., preferably at approximately 45° C.

A further subject of the present invention is pemetrexed diethyl ester 2 obtainable by the above-mentioned process.

A further subject of the present invention is pemetrexed diethyl ester 2 in crystalline form. Pemetrexed diethyl ester 2 in crystalline form is preferably characterized by a purity greater than 99.0% by weight.

The purity of pemetrexed diethyl ester 2 can be evaluated by methods known in the art. By way of example, an HPLC method used during the development of the process according to the present invention is given below.

Operating Conditions
Instrument:
SHIMADZU HPLC: LC-10AD
UV Detector: SPD 10AVP
auto-sampler: SIL-ADVP
Wavelength: 254 nm
Column:
 column: Halo C18
 length: 150 mm
 Inside diameter: 4.6 mm
 particle size: 2.7 µm
 (HALO Cat.N. 92814-702 or equivalent)
Injection volume: 5 µl
Column temperature: 30±1° C.
Sample temperature: Ambient temperature
Flow: 0.4 ml/min
Mobile phases: Eluant A: 0.3% v/v trifluoroacetic acid in water for HPLC
 Eluant B: acetonitrile
Run time: 45 minutes (including reconditioning)
Diluent: acetonitrile-water for HPLC=1:1
Blank: injection of diluent only is used as blank
Run: gradient
Gradient programme:

GRADIENT PROGRAMME

| Time (min) | Eluant A % (v/v) | Eluant B % (v/v) |
| --- | --- | --- |
| 00 | 85 | 15 |
| 2 | 85 | 15 |
| 15 | 60 | 40 |
| 30 | 60 | 40 |
| 35 | 85 | 15 |
| 36 | 85 | 15 |
| 45 (end of run) | 85 | 15 |

Figure 1:
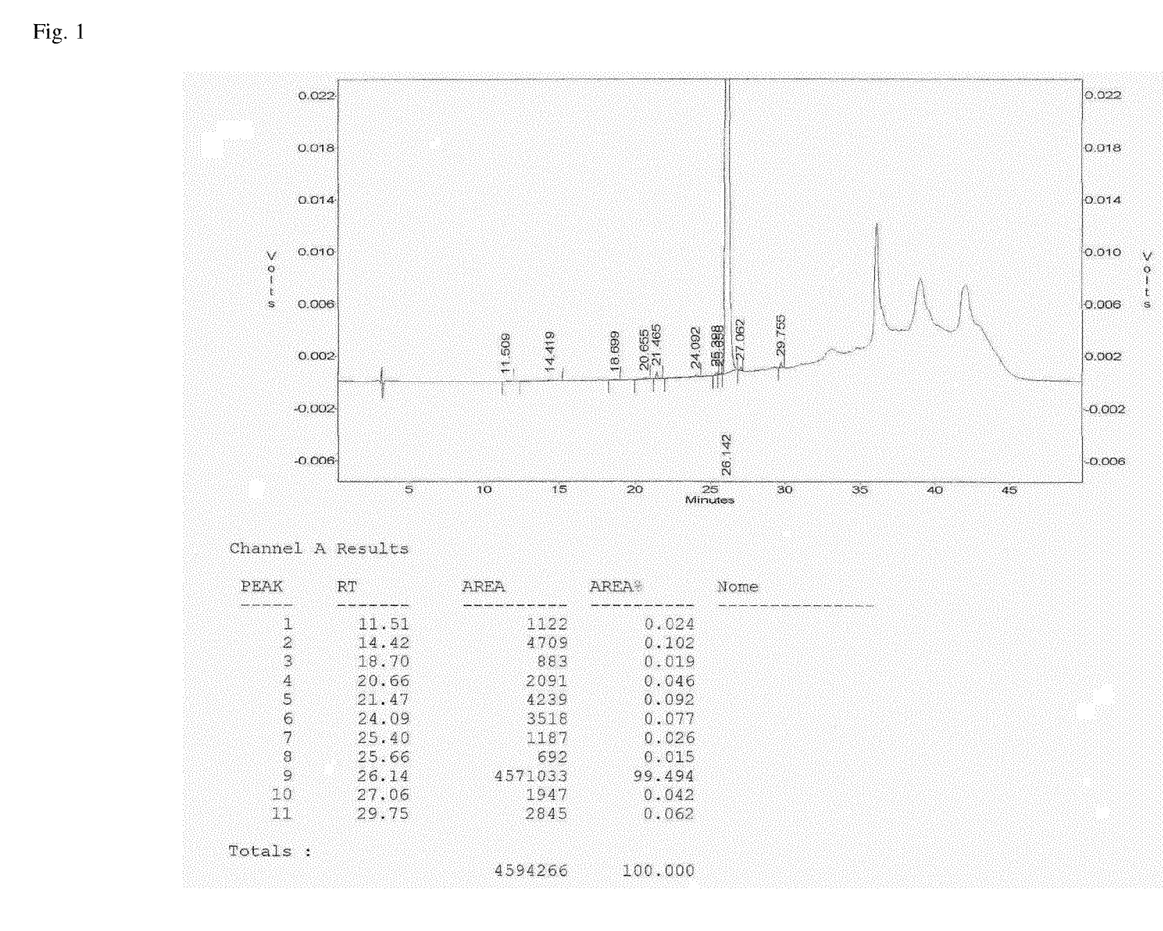
FIG. 1 shows the HPLC profile of pemetrexed diethyl ester 2.

FIG. 1 shows the HPLC purity profile obtained by analyzing pemetrexed diethyl ester 2 obtained in accordance with the process of the present invention by means of the analytical method described above.

Pemetrexed diethyl ester 2 in crystalline form is also preferably characterized by a PXRD diffractogram, the characteristic peaks of which are given in Table 1.

TABLE 1

| Pos. [°2Th.] | Height [cts] | FWHM [°2Th.] | d-spacing [Å] | Rel. Int. [%] |
| --- | --- | --- | --- | --- |
| 3.4828 | 7322.70 | 0.1673 | 25.36968 | 100.00 |
| 4.3175 | 2851.38 | 0.2676 | 20.46636 | 38.94 |
| 6.3201 | 165.18 | 0.2007 | 13.98519 | 2.26 |
| 6.8751 | 581.56 | 0.0836 | 12.85747 | 7.94 |
| 7.8339 | 724.89 | 0.1338 | 11.28584 | 9.90 |
| 8.5069 | 433.23 | 0.2676 | 10.39445 | 5.92 |
| 9.2030 | 2302.68 | 0.0836 | 9.60968 | 31.45 |
| 9.3205 | 2917.11 | 0.1171 | 9.48880 | 39.84 |
| 10.3643 | 5158.79 | 0.2342 | 8.53536 | 70.45 |
| 10.8300 | 306.65 | 0.1004 | 8.16942 | 4.19 |
| 11.5531 | 279.84 | 0.1004 | 7.65966 | 3.82 |
| 12.8317 | 264.06 | 0.1338 | 6.89914 | 3.61 |
| 13.8636 | 742.97 | 0.2676 | 6.38787 | 10.15 |
| 14.8857 | 424.56 | 0.2007 | 5.95146 | 5.80 |
| 15.7007 | 102.17 | 0.2676 | 5.64434 | 1.40 |
| 16.6393 | 769.08 | 0.1004 | 5.32799 | 10.50 |
| 17.4957 | 437.48 | 0.1673 | 5.06907 | 5.97 |
| 18.5451 | 807.29 | 0.2342 | 4.78454 | 11.02 |
| 19.7584 | 894.19 | 0.1338 | 4.49339 | 12.21 |
| 21.2950 | 406.77 | 0.1673 | 4.17249 | 5.55 |
| 21.7516 | 506.19 | 0.3011 | 4.08593 | 6.91 |
| 22.8449 | 285.82 | 0.2342 | 3.89281 | 3.90 |
| 23.5787 | 166.50 | 0.2676 | 3.77330 | 2.27 |
| 24.4555 | 172.28 | 0.2676 | 3.63996 | 2.35 |
| 24.9439 | 141.55 | 0.2007 | 3.56979 | 1.93 |
| 25.3845 | 135.00 | 0.2007 | 3.50881 | 1.84 |
| 26.6139 | 297.79 | 0.2342 | 3.34946 | 4.07 |
| 28.8597 | 71.07 | 0.4015 | 3.09372 | 0.97 |
| 29.5835 | 615.24 | 0.1004 | 3.01965 | 8.40 |
| 31.0042 | 66.51 | 0.2007 | 2.88445 | 0.91 |
| 33.3343 | 25.21 | 0.6691 | 2.68796 | 0.34 |
| 35.3382 | 28.02 | 0.5353 | 2.53999 | 0.38 |

Figure 2:
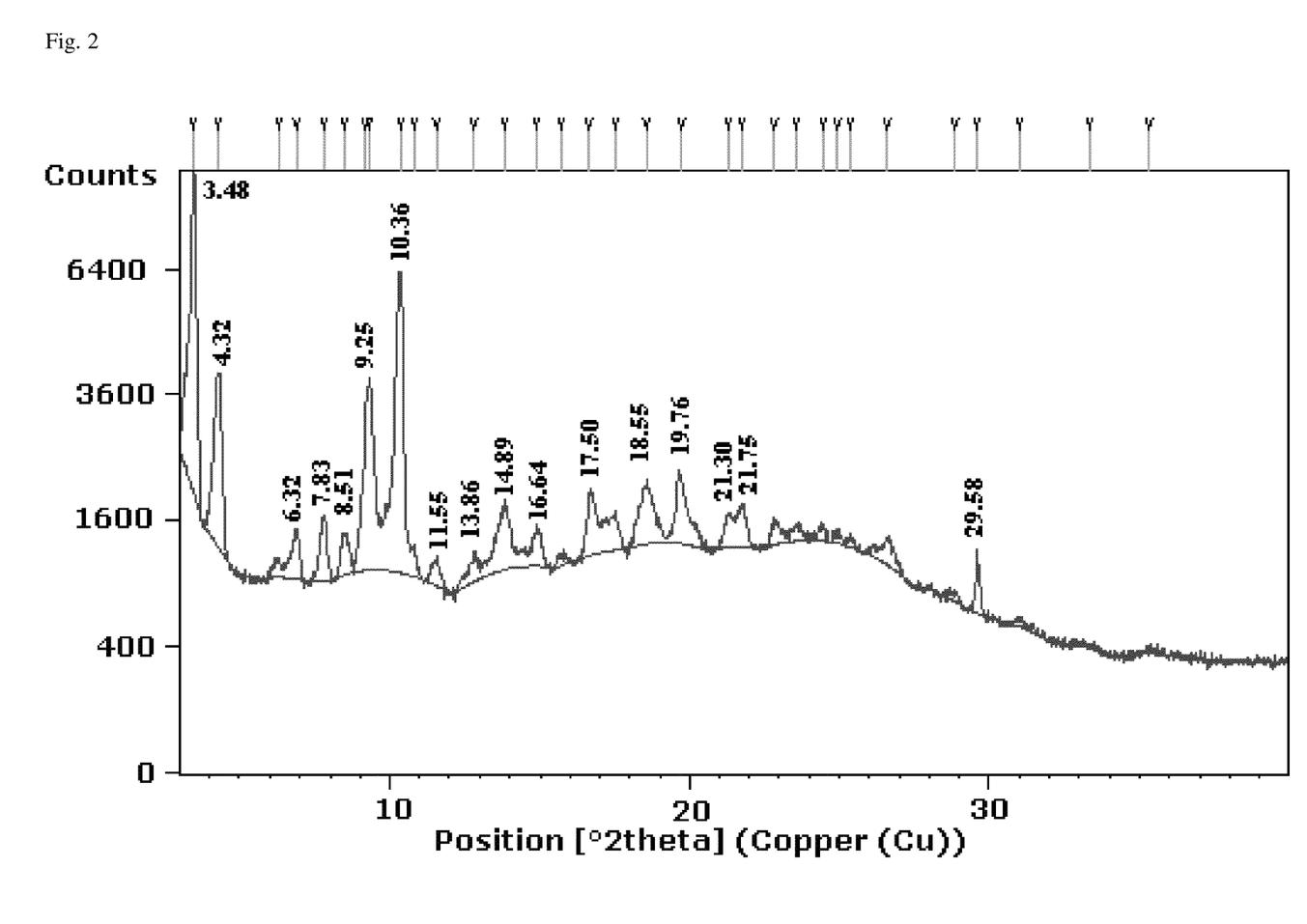
FIG. 2 shows the PXRD diffractogram of pemetrexed diethyl ester 2.

In particular, pemetrexed diethyl ester 2 in crystalline form is characterized by a PXRD diffractogram which comprises the following principal peaks: 3.48; 4.32; 6.32; 6.88; 7.83; 8.51; 9.25; 10.36; 11.55; 13.86; 14.89; 16.64; 17.50; 18.55; 19.76; 21.30; 21.75; 29.58±0.1 2theta, preferably by a PXRD diffractogram as shown in FIG. 2.

Figure 3:
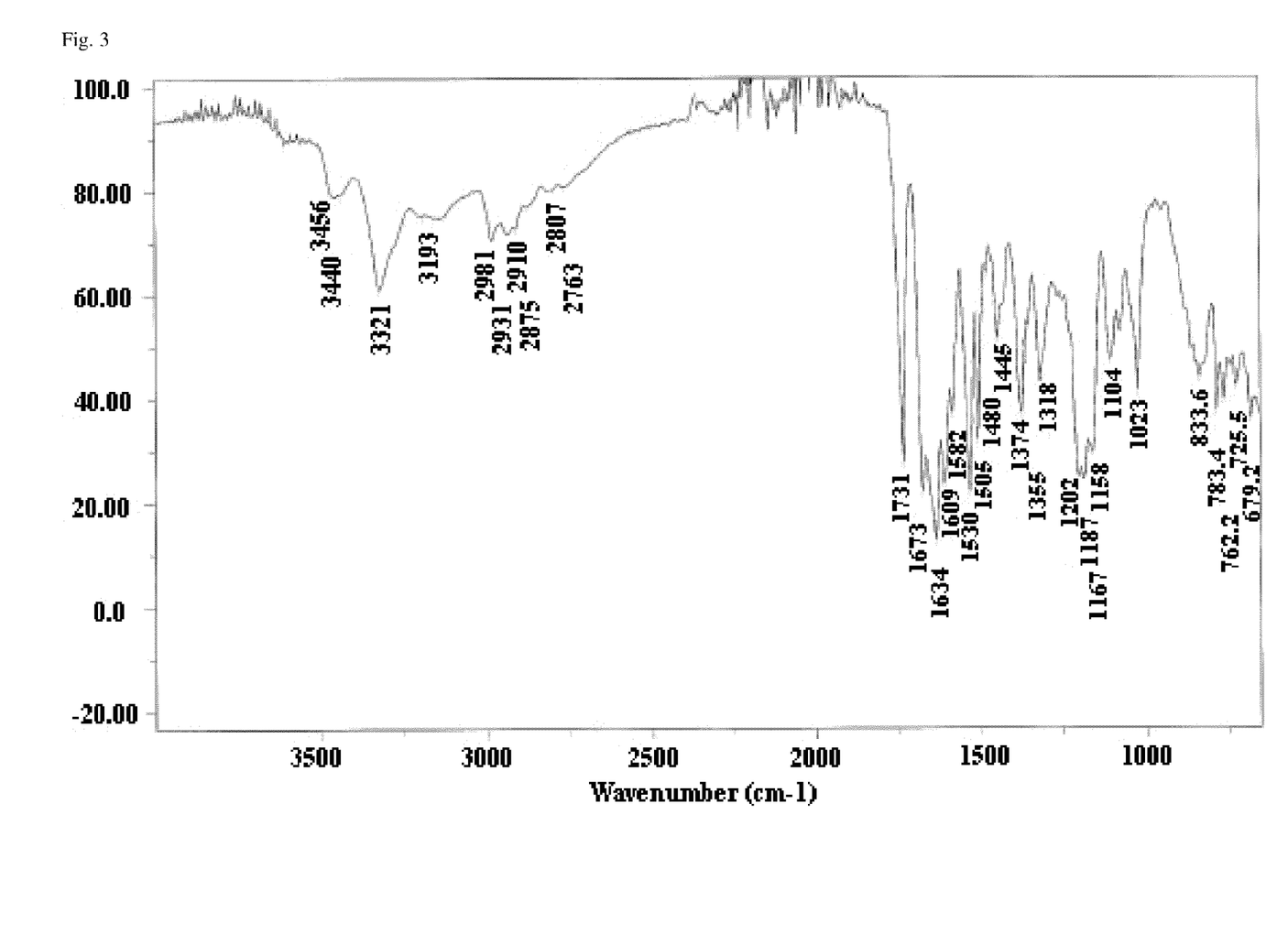
FIG. 3 shows the FT-IR profile of pemetrexed diethyl ester 2.

Pemetrexed diethyl ester 2 in crystalline form is also characterized by an FT-IR profile which comprises the following principal peaks: 3456; 3440; 3321; 3193; 2981; 2931; 2910; 2875; 2807; 2763; 1731; 1673; 1634; 1609; 1582; 1530; 1505; 1480; 1445; 1374; 1355; 1318; 1202; 1187; 1167; 1158; 1104; 1023; 833.6; 783.4; 762.2; 725.5; 679.2±2 cm$^{-1}$, preferably by an FT-IR profile as shown in FIG. 3.

Figure 4:
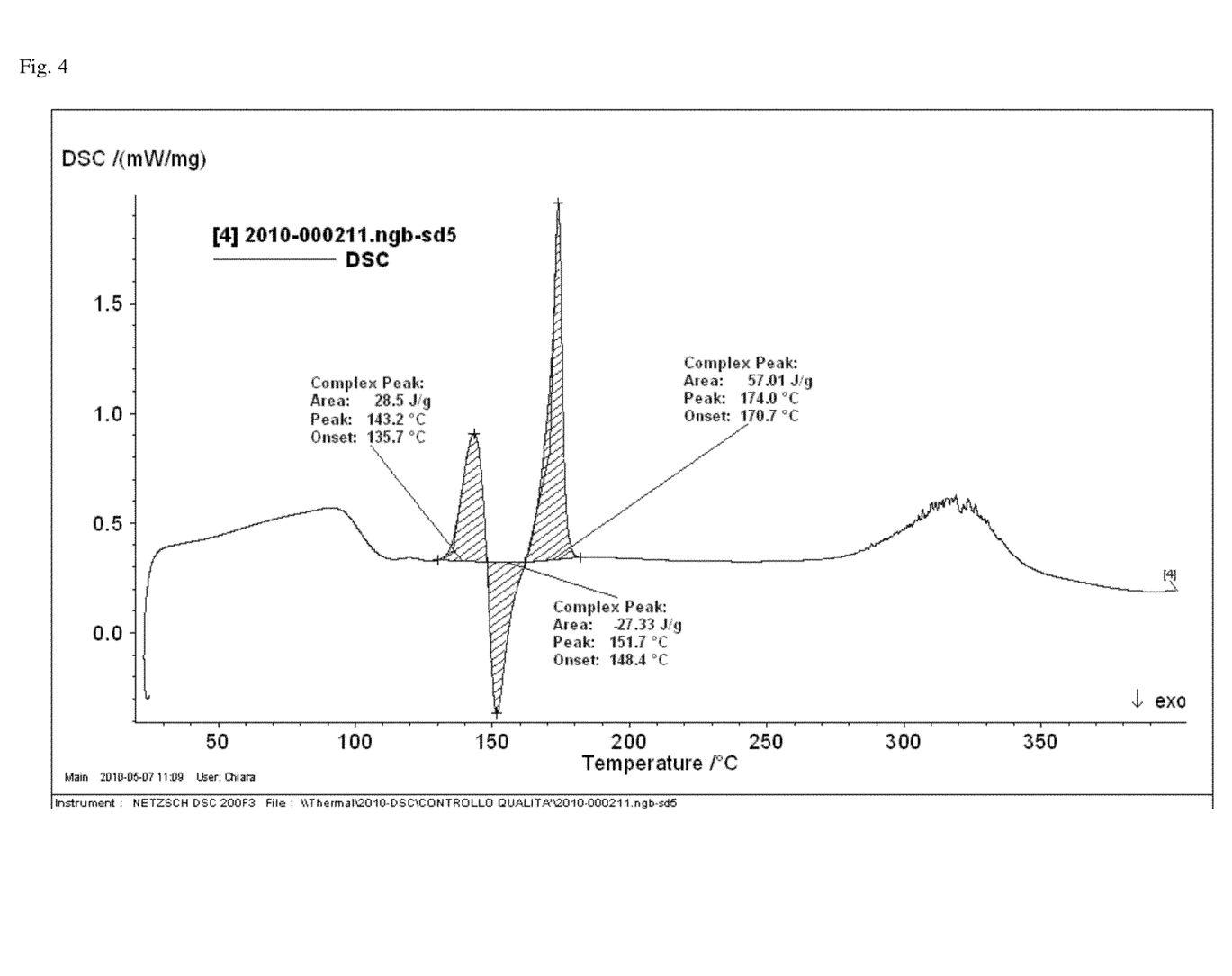
FIG. 4 shows the DSC profile of pemetrexed diethyl ester 2 in crystalline form.
Figure 5:
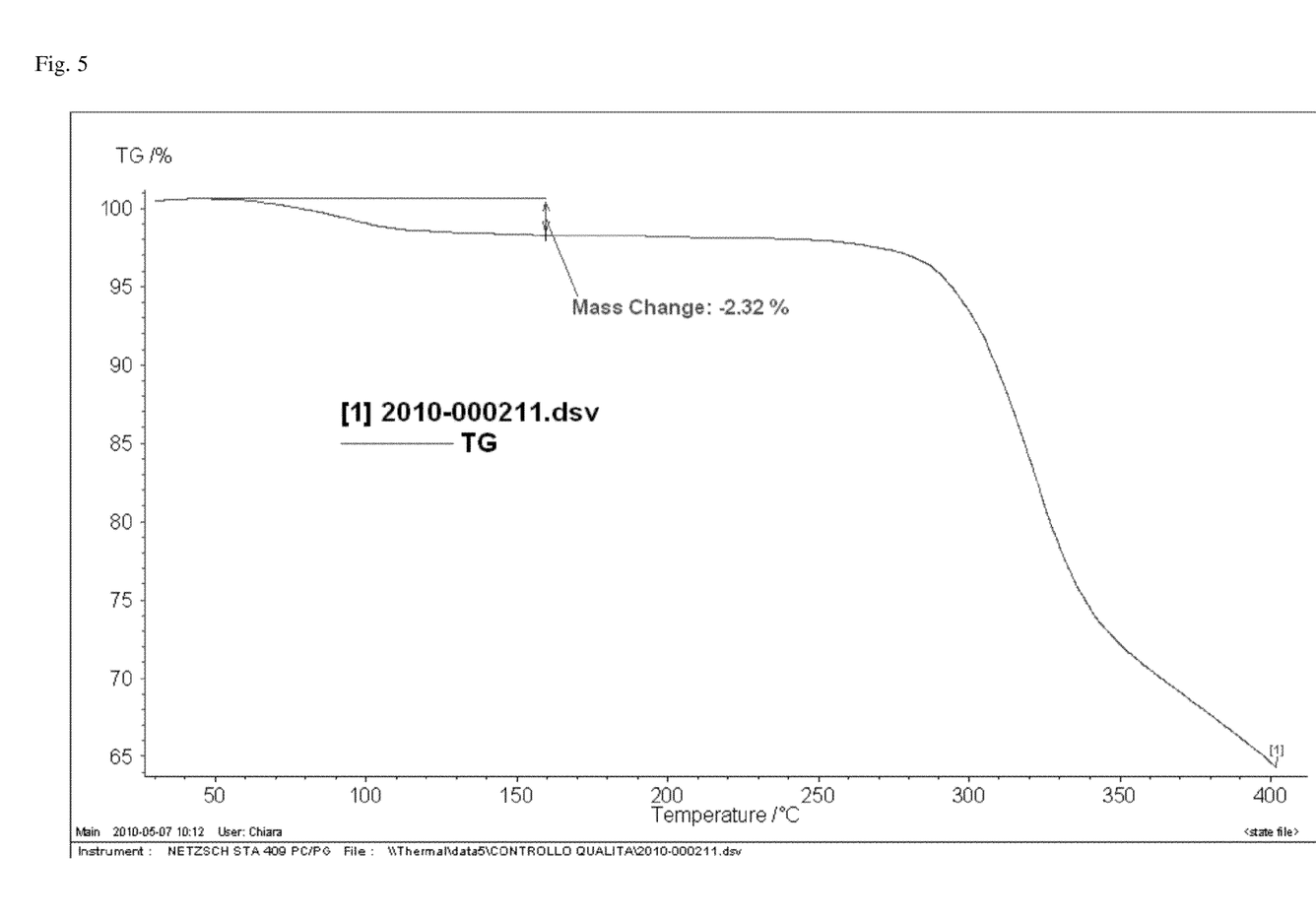
FIG. 5 shows the TGA profile of pemetrexed diethyl ester 2 in crystalline form.

Pemetrexed diethyl ester 2 in crystalline form is further characterized by a DSC profile which shows an exothermic peak at 143.2° C. with an onset at 135.7° C.; an endothermic peak at 151.7° C. with an onset at 148.4° C.; an exothermic peak at 174.0° C. with an onset at 170.7° C., preferably by a DSC profile as shown in FIG. 4 and/or by a TGA profile preferably as shown in FIG. 5.

It was then surprisingly found that the production, by means of the process of the invention, of pemetrexed diethyl ester 2 in crystalline form with a purity greater than 99.0% by weight enables it to be used as such for the production of the pemetrexed disodium salt 5; that is to say, without having to purify it, as known in the art, by the preparation of derivatives or salts, such as, for example, the salt of p-toluenesulphonic acid.

It was then unexpectedly found that the availability of pemetrexed diethyl ester 2 in crystalline form with a high degree of purity enables the pemetrexed disodium salt 5 to be obtained by a single synthesis step, with a quality complying with the requirements demanded of an active ingredient.

In the methods described in the literature, starting from pemetrexed diethyl ester in the form of a salt of p-toluenesulphonic acid 3, first of all the pemetrexed is isolated in acid form 4 and then the pemetrexed disodium salt 5 is isolated, as indicated in Scheme 1.

In the process for the production of the pemetrexed disodium salt 5 according to the present invention, the fact that p-toluenesulphonic acid is not used is an advantage over the prior art because it enables the formation of p-toluenesulphonic acid esters as possible by-products to be avoided. In fact, the esters of arylsulphonic and alkylsulphonic acids, such as precisely those of para-toluenesulphonic acid, are alkylating substances classified as genotoxic which are formed from the respective acids by reaction with alcohols. Their content is reduced to within very low limits in a pharmaceutical active ingredient (see *Genotoxic and carcinogenic impurities in drug substances: recommended approaches FDA* 2008).

Therefore, a further subject of the present invention is a process for the preparation of the disodium salt 5

5 comprising the above-mentioned process for the preparation of pemetrexed diethyl ester 2.

In a preferred embodiment of the present invention, the process for the preparation of the disodium salt 5 comprises the following steps:

e) dissolving the pemetrexed diethyl ester 2 in a protic polar organic solvent and/or a mixture of protic polar organic solvents and f) subsequent hydrolysis.

According to the invention, the protic polar organic solvent is preferably a $C_1$-$C_4$ alcohol, more preferably ethanol.

According to the invention, the hydrolysis is preferably a basic hydrolysis, more preferably a basic hydrolysis carried out with an aqueous solution of a basic sodium salt, even more preferably of sodium hydroxide.

The aqueous solution has a pH of preferably from 10 to 13, more preferably from 12 to 13.

A further subject of the present invention is the pemetrexed disodium salt 5 obtainable by means of the above-mentioned process.

A further subject of the present invention is the pemetrexed disodium salt 5 having a purity preferably greater than 99.7%.

The purity of the pemetrexed disodium salt 5 can be evaluated by means of methods known in the art. By way of example, it is possible to use the same HPLC method as that given above for analyzing pemetrexed diethyl ester 2.

Figure 6:
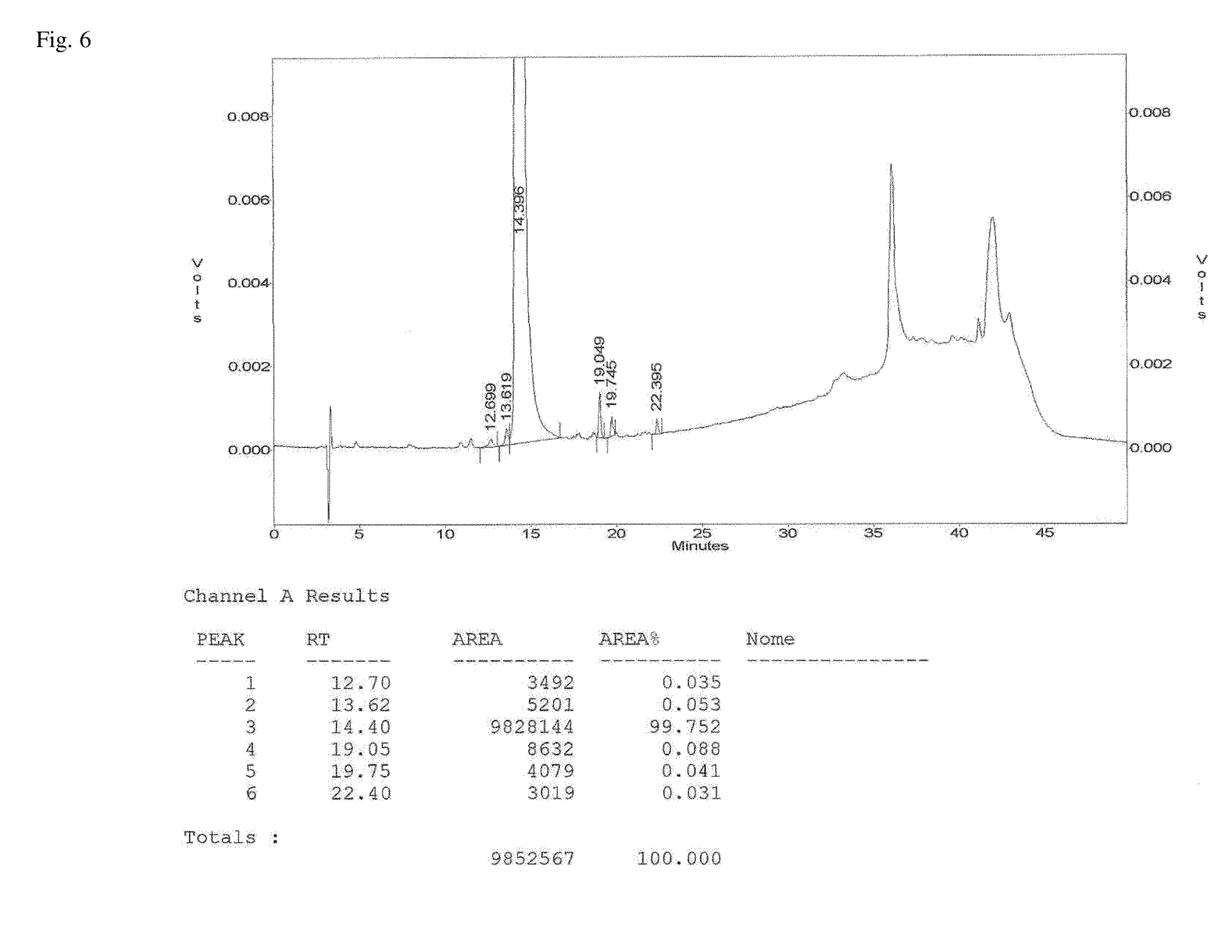
FIG. 6 shows the profile of the chromatogram obtained by analyzing pemetrexed disodium salt.

FIG. 6 shows the profile of the chromatogram which is obtained by analyzing pemetrexed disodium salt 5 obtained by means of the process according to the present invention by the HPLC method described.

According to a preferred aspect of the invention, from 5 to 8 volumes of protic polar organic solvent (ml), preferably from 6 to 7, are used to 1 part by weight of pemetrexed diethyl ester 2 (g).

According to a further preferred aspect of the invention, from 0.5 to 2 volumes of basic aqueous solution (ml), preferably from 0.7 to 1.3, are used per volume of polar organic solvent (ml).

The ability to obtain pemetrexed disodium salt 5 of a quality suitable for an active ingredient in a single step starting from pemetrexed diethyl ester 2 enables a shorter process to be created with fewer operations involving the handling of cytotoxic compounds and a reduced likelihood of coming up against phenomena degrading the product (which is sensitive to air), which could have a detrimental effect on the quality thereof.

The following Examples provide a detailed illustration of the process to which the present invention relates and do not in any way constitute a limitation thereof.

EXAMPLES

Example 1

Preparation of pemetrexed diethyl ester 2 (diethyl ester of N-[4-[2-(2-amino-4,7-dihydro-4-oxo-1H-pyrrolo[2,3-d]pyrimidin-5-yl)ethyl]benzoyl]-L-glutamic acid)

200 ml of dimethylformamide, followed by 200 ml of dichloromethane and 18.5 g of N-methylmorpholine, were added to 50 g of 4-[2-(2-amino-4,7-dihydro-4-oxo-1H-pyrrolo[2,3-d]pyrimidin-5-yl)ethyl]benzoic acid introduced into a 2000 ml flask maintained under a nitrogen atmosphere. The temperature of the mixture obtained was brought to 5±2° C. and a separately prepared solution composed of 31.7 g of 2-chloro-4,6-dimethoxy-1,3,5-triazine, 100 ml of dimethylformamide and 200 ml of dichloromethane was added thereto over a period of approximately one hour, while maintaining the temperature at 5±2° C. The temperature was then maintained at 5±2° C. for a further hour and, while still maintaining it at 5±2° C., a solution composed of 43.5 g of L-glutamic acid diethyl ester hydrochloride in 100 ml of dimethylformamide was added over a period of approximately 40 minutes. Immediately after this addition, 18.5 g of N-methylmorpholine were poured into the reaction mixture. The temperature was allowed to rise to 20±2° C. over a period of approximately 30 minutes, those conditions being maintained for three hours. 500 ml of dichloromethane were then added to the reaction mixture and the mixture obtained was poured onto a solution composed of 500 ml of deionized water and 500 ml of a 10% sodium bicarbonate solution, over a period of approximately 15 minutes. The whole was agitated at 20±2° C. for 10 minutes, and then the phases were left to separate. The lower organic phase was washed in sequence with 500 ml of deionized water, 500 ml of 10% aqueous sodium bicarbonate solution and 1000 ml of deionized water. The organic phase obtained was evaporated to give a readily agitatable oil (weight of the residue 390 g). 1000 ml of absolute ethanol were added to the residue and the solvent was distilled to give a readily agitatable oil (weight of the residue 185 g). 640 ml of absolute ethanol were poured onto this residue and the mixture was heated to 60-65° C. to give a clear solution. Over a period of approximately 2 hours, the solution was cooled from 60-65° C. to 5° C., agitation being maintained at that temperature for 4 hours. At approximately 45° C., a white solid started to precipitate. When maintenance at 5° C. was terminated, the solid obtained was filtered off over a Gooch filter and washed with two portions of 50 ml of absolute ethanol at 5° C. After drying at 60° C. under vacuum (1 mbar) for 16 hours, 48.3 g of the expected product were obtained (yield 63%).

The product obtained was analyzed by PXRD, DSC, TGA and IR and the data obtained can be superimposed on those of FIGS. 1, 2, 3 and 4, relating to the crystalline form of the diethyl ester of N-[4-[2-(2-amino-4,7-dihydro-4-oxo-1H-pyrrolo[2,3-d]pyrimidin-5-yl)ethyl]benzoyl]-L-glutamic acid. The HPLC purity of the product obtained was greater than 99.0%.

Example 2

Preparation of the pemetrexed disodium salt 5 (disodium salt of N-[4-[2-(2-amino-4,7-dihydro-4-oxo-1H-pyrrolo[2,3-d]pyrimidin-5-yl)ethyl]benzoyl]-L-glutamic acid)

56 g of the diethyl ester of N-[4-[2-(2-amino-4,7-dihydro-4-oxo-1H-pyrrolo[2,3-d]pyrimidin-5-yl)ethyl]benzoyl]-L-glutamic acid and 360 ml of degassed absolute ethanol were introduced into a 2000 ml flask.

The mixture was placed under agitation at 20±2° C. and 360 ml of a 1M aqueous sodium hydroxide solution (prepared from degassed deionized water and sodium hydroxide beads) were added thereto over a period of approximately 10 minutes.

The mixture was maintained under agitation at 20±2° C. for three hours, the complete solubilization of the solid being observed, and then, still at 20±2° C., a 1M aqueous HCl solution was added until the pH of the mixture reached a value of 8.1±0.1 (approximately 100 ml). The mixture was filtered over a 0.45 micron filter and 900 ml of degassed absolute ethanol and 125 ml of degassed deionized water were added to the filtrate. The filtrate was heated to 55° C. and maintained under those conditions for 10 minutes. The solution was then cooled to 20±2° C. over a period of approximately one hour and the suspension so obtained was maintained under agitation for a further 16 hours. The precipitate obtained was then filtered off and washed with two portions of 200 ml of degassed absolute ethanol. The solid was discharged and dried under vacuum (1 mbar) at 60° C. for 3 hours. 54 g of pemetrexed disodium salt 5 were thus obtained (yield 90%).

The purity of the product evaluated by HPLC was greater than 99.7%.

The invention claimed is:
1. A process for the preparation of pemetrexed diethyl ester 2 in solid crystalline form which comprises:
reacting compounds 1 and 1a in the presence of a chemical agent capable of promoting the formation of a peptide bond in an aprotic organic solvent to obtain a mixture, said chemical agent being selected from the group consisting of
2-chloro-4,6-dimethoxy-1,3,5-triazine

N,N'-dicyclohexylcarbodiimide, hydroxybenzotriazole, and 1-ethyl-3-(3-dimethylaminopropyl) carbodiimide and
purifying said mixture,
wherein the mixture is subjected to the following steps:
a) washing with a basic aqueous solution;
b) concentration of the organic phase;
c) addition of a polar organic solvent and/or a mixture of polar organic solvents;
d) precipitation of the pemetrexed diethyl ester 2 in solid crystalline form.

2. The process according to claim 1, wherein the basic aqueous solution has a pH of from 7 to 10.

3. The process according to claim 2, wherein the basic aqueous solution has a pH greater than 7 and less than or equal to 8.

4. The process according to claim 1, wherein that the polar organic solvent is a $C_1$-$C_4$ alcohol, an aliphatic or aromatic ketone, dimethyl sulphoxide or mixtures thereof.

5. The process according to claim 1, wherein the polar organic solvent is ethanol.

6. The process according to claim 1, wherein the precipitation is effected by heating the mixture obtained in step c) to a temperature of from 50 to 80° C., and then cooling it to a temperature of from 0 to 10° C.

7. The process according to claim 6, wherein the mixture obtained in step c) is heated to a temperature from 60 to 65° C., and cooled to a temperature of from 0 to 10° C.

8. The process according to claim 1, wherein the precipitation takes place at a temperature of from 30 to 60° C.

9. The process according to claim 8, wherein the precipitation takes place at a temperature of 45° C.

10. A process for the preparation of the disodium salt 5 comprising a process for the preparation of pemetrexed diethyl ester 2 according to claim 1.

11. The process for the preparation of the disodium salt 5 according to claim 10, comprising the following steps:
a) dissolving the pemetrexed diethyl ester 2 in a protic polar organic solvent and/or a mixture of protic polar organic solvents and
b) subsequently hydrolysing.

12. The process according to claim 11, wherein the protic polar organic solvent is a $C_1$-$C_4$ alcohol.

13. The process according to claim 11, wherein the protic polar organic solvent is ethanol.

14. The process according to claim 11, wherein the hydrolysing step is a basic hydrolysis.

15. The process according to claim 14, wherein the hydrolysing step is obtained with an aqueous solution having a pH of from 10 to 13.

16. The process according to claim 14, wherein the hydrolysing step is obtained with an aqueous solution having a pH of from 12 to 13.

17. Pemetrexed diethyl ester 2 in crystalline form.

18. The pemetrexed diethyl ester 2 crystalline form according to claim 17, with a purity greater than 99.0% by weight.

19. The pemetrexed diethyl ester 2 crystalline form according to claim 17, characterized by a PXRD diffractogram which comprises the following principal peaks: 3.48; 4.32; 6.32; 6.88; 7.83; 8.51; 9.25; 10.36; 11.55; 13.86; 14.89; 16.64; 17.50; 18.55; 19.76; 21.30; 21.75; 29.58±0.1 2theta, or by a PXRD diffractogram as shown in FIG. 2.

20. The pemetrexed diethyl ester 2 crystalline form according to claim 17, characterized by an FT-IR profile which comprises the following principal peaks: 3456; 3440; 3321; 3193; 2981; 2931; 2910; 2875; 2807; 2763; 1731; 1673; 1634; 1609; 1582; 1530; 1505; 1480; 1445; 1374; 1355; 1318; 1202; 1187; 1167; 1158; 1104; 1023; 833.6; 783.4; 762.2; 725.5; 679.2±2 cm$^{-1}$, or by an FT-IR profile as shown in FIG. 3.

21. The pemetrexed diethyl ester 2 crystalline form according to claim 17, characterized by a DSC profile which shows an exothermic peak at 143.2° C. with an onset at 135.7° C.; an endothermic peak at 151.7° C. with an onset at 148.4° C.; an exothermic peak at 174.0° C. with an onset at 170.7° C., or by a DSC profile as shown in FIG. 4.

22. The pemetrexed diethyl ester 2 crystalline form according to claim 17, characterized by a TGA profile as shown in FIG. 5.

* * * * *

UNITED STATES PATENT AND TRADEMARK OFFICE
CERTIFICATE OF CORRECTION

PATENT NO. : 8,981,090 B2  
APPLICATION NO. : 13/176199  
DATED : March 17, 2015  
INVENTOR(S) : Ciambecchini et al.

Page 1 of 1

It is certified that error appears in the above-identified patent and that said Letters Patent is hereby corrected as shown below:

On the Title Page

Column 1, item (75) Inventors:

Umberto Ciambecchini, Patricia (IT) should read "Umberto Ciambecchini, Patrica (IT)"

Stefano Turchetta, Patricia (IT) should read "Stefano Turchetta, Patrica (IT)"

Mauzio Zenoni, Patricia (IT) should read "Maurizio Zenoni, Patrica (IT)"

Lorenzo De Ferra, Patricia (IT) should read "Lorenzo De Ferra, Patrica (IT)"

Paolo Brandi, Patricia (IT) should read "Paolo Brandi, Patrica (IT)"

Signed and Sealed this  
Seventh Day of July, 2015

Michelle K. Lee  
*Director of the United States Patent and Trademark Office*